US00PP11756P2

(12) United States Plant Patent
VandenBerg

(10) Patent No.: US PP11,756 P2
(45) Date of Patent: Jan. 30, 2001

(54) CHRYSANTHEMUM PLANT NAMED 'YOLAFAYETTE'

(75) Inventor: Cornelis P. VandenBerg, Salinas, CA (US)

(73) Assignee: Yoder Brothers, Inc., Barberton, OH (US)

( * ) Notice: Under 35 U.S.C. 154(b), the term of this patent shall be extended for 0 days.

(21) Appl. No.: 09/270,784

(22) Filed: Mar. 17, 1999

(51) Int. Cl.[7] ..... A01H 5/00
(52) U.S. Cl. ..... Plt./295
(58) Field of Search ..... Plt./295

*Primary Examiner*—Howard J. Locker
(74) *Attorney, Agent, or Firm*—C. A. Whealy

(57) ABSTRACT

A distinctive cultivar of Chrysanthemum plant named 'Yolafayette', characterized by its upright, broadly spreading and uniformly mounded plant habit; freely branching habit; excellent plant strength; small dark green leaves; uniform and early flowering; numerous daisy-type inflorescences that are about 4.2 cm in diameter; bright yellow-colored ray florets and darker yellow disc florets; and excellent postproduction longevity with inflorescences and leaves maintaining good substance and color for about three or four weeks in an interior environment.

2 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name Yolafayette.

The new Chrysanthemum is a product of a planned breeding program conducted by the Inventor in Salinas, Calif. The objective of the breeding program is to create new pot-type Chrysanthemum cultivars having desirable inflorescence forms and floret colors and good post-production longevity.

The new Chrysanthemum originated from a cross made by the Inventor in July, 1993, in Salinas, Calif., of the *Dendranthema grandiflora* cultivar Forge, disclosed in U.S. Plant Pat. No. 7,470, as the female, or seed, parent, with a proprietary Chrysanthemum seedling selection identified as code number YB-6709, as the male, or pollen, parent.

The new Chrysanthemum was discovered and selected by the Inventor as a flowering plant within the progeny of the stated cross in a controlled environment in Salinas, Calif., in February, 1994. The selection of this plant was based on its desirable inflorescence form and floret colors and good post-production longevity.

Asexual reproduction of the new Chrysanthemum by terminal cuttings harvested in a controlled environment in Salinas, Calif., has shown that the unique features of this new Chrysanthemum are stable and reproduced true to type in successive generations.

SUMMARY OF THE INVENTION

The cultivar Yolafayette has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yolafayette'. These characteristics in combination distinguish 'Yolafayette' as a new and distinct Chrysanthemum:

1. Upright, broadly spreading and uniformly mounded plant habit.
2. Freely branching habit, very full and dense plants.
3. Excellent plant strength.
4. Small dark green leaves.
5. Uniform and early flowering.
6. Floriferous with numerous daisy-type inflorescences that are about 4.2 cm in diameter.
7. Bright yellow-colored ray florets and darker yellow disc florets.
8. Excellent postproduction longevity with inflorescences and leaves maintaining good substance and color for about three or four weeks in an interior environment.

The new Chrysanthemum can be compared to the Chrysanthemum cultivar Yellow Davis, disclosed in U.S. Plant Pat. No. 9.559. However in side-by-side comparisons in Salinas, Calif., and Leamington, Ontario, Canada, under commercial practice, plants of the new Chrysanthemum differ from plants of the cultivar Yellow Davis in the following characteristics:

1. Plants of the new Chrysanthemum are more outwardly spreading, stronger and more freely branching than plants of the variety Yellow Davis.
2. Leaves of the new Chrysanthemum are smaller, darker green, and less susceptible to foliar flecking than leaves of the variety Yellow Davis.
3. Plants of the new Chrysanthemum flower about one week earlier than plants of the variety Yellow Davis.
4. Plants of the new Chrysanthemum have smaller inflorescences than plants of the variety Yellow Davis.
5. Plants of the new Chrysanthemum have darker yellow ray florets than plants of the variety Yellow Davis.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type.

The photograph at the top of the first sheet comprises a side perspective view of a typical flowering plant of 'Yolafayette'.

The photograph at the bottom of the first sheet comprises a close-up view of upper (left) and lower (right) surfaces of typical inflorescences and upper (left) and lower (right) surfaces of typical leaves of the cultivar Yolafayette.

The photograph at the top of the second sheet comprises a side perspective view of typical flowering plants of 'Yolafayette' (left) and 'Yellow Davis' (right).

The photograph at the bottom of the second sheet comprises a close-up view of upper surfaces of typical inflorescences and leaves of plants of 'Yolafayette' (left) and 'Yellow Davis' (right). Floret and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., and Leamington, Ontario, Canada, under greenhouse conditions which approximate those generally used in commercial potted Chrysanthemum production. Four unrooted cuttings were directly stuck in a 15-cm container and pinched once. Plants used for this description were grown as spray-types. Measurements and numerical values represent averages of typical flowering plants.

Botanical classification: *Dendranthema grandiflora* cultivar Yolafayette.

Commercial classification: Daisy spray-type pot Chrysanthemum.

Parentage:

*Female or seed parent.*—*Dendranthema grandiflora* cultivar Forge, disclosed in U.S. Plant Pat. No. 7,470.

*Male or pollen parent.*—Proprietary *Dendranthema grandiflora* seedling selection identified as code number YB-6709.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous daisy pot Chrysanthemum typically grown as a spray-type. Inverted triangle; stems broadly spreading; uniformly mounded plant habit. Excellent plant strength. Freely branching; about five or six lateral branches develop after removal of terminal apex (pinching); very dense and full plants.

*Plant height.*—About 31 cm.

*Plant width.*—About 46 cm.

*Stem color.*—Greener than 147A.

*Stem texture.*—Pubescent.

*Foliage description.*—Arrangement: Alternate. Length: About 5.1 cm. Width: About 3.5 cm. Apex: Mucronate. Base: Attenuate. Margin: Palmately lobed, sinuses between lateral lobes mostly parallel. Texture: Upper and lower surfaces with very fine pubescence; veins prominent on lower surface. Petiole length: About 1.7 cm. Color: Young foliage upper surface: 147A. Young foliage lower surface: 147B. Mature foliage upper surface: 147A. Mature foliage lower surface: 147B. Venation upper surface: 147A. Venation lower surface: 147B.

Inflorescence description:

*Appearance.*—Daisy inflorescence form with oblong-shaped ray florets. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 7.5 to 8 weeks later.

*Postproduction longevity.*—Inflorescences and leaves will maintain good color and substance for about three or four weeks in an interior environment.

*Quantity of inflorescences.*—Very floriferous; about 12 inflorescences per lateral branch or about 66 inflorescences per plant.

*Inflorescence bud.*—Height: About 5 mm. Diameter: About 7 mm. Color: Close to 141A.

*Inflorescence size.*—Diameter: About 4.2 cm. Depth (height): About 1.2 cm. Diameter of disc: About 1.6 cm.

*Ray florets.*—Shape: Oblong with short corolla tube. Orientation: Perpendicular to peduncle. Aspect: Straight; flat to slightly concave. Length: About 2.1 cm. Width: About 7 mm. Apex: Emarginate. Margin: Entire. Texture: Smooth, glabrous. Number of ray florets per inflorescence: About 24. Color: When opening: Yellow, 9A. Fully opened, upper surface: Yellow, 9A. Fully opened, lower surface: Yellow, 9A–9B to 8A.

*Disc florets.*—Shape: Tubular, enlarged. Apex: Serrated. Length: About 8 mm. Width: Apex: About 2 mm. Base: About 1 mm. Number of disc florets per inflorescence: Numerous, about 124. Color: Immature: 154A. Mature: Apex: 12A. Mid-section: Light green. Base: White, 155D.

*Peduncles.*—Aspect: Angled about 45° to stem. Strength: Strong, but flexible. Length: First peduncle: About 5.7 cm. Fourth peduncle: About 8.4 cm. Texture: Pubescent. Color: Greener than 147A.

*Reproductive organs.*—Androecium: Present on disc florets only. Anther color: 13A. Pollen: Amount: Scarce. Color: 14A. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Yolafayette', as illustrated and described.

* * * * *

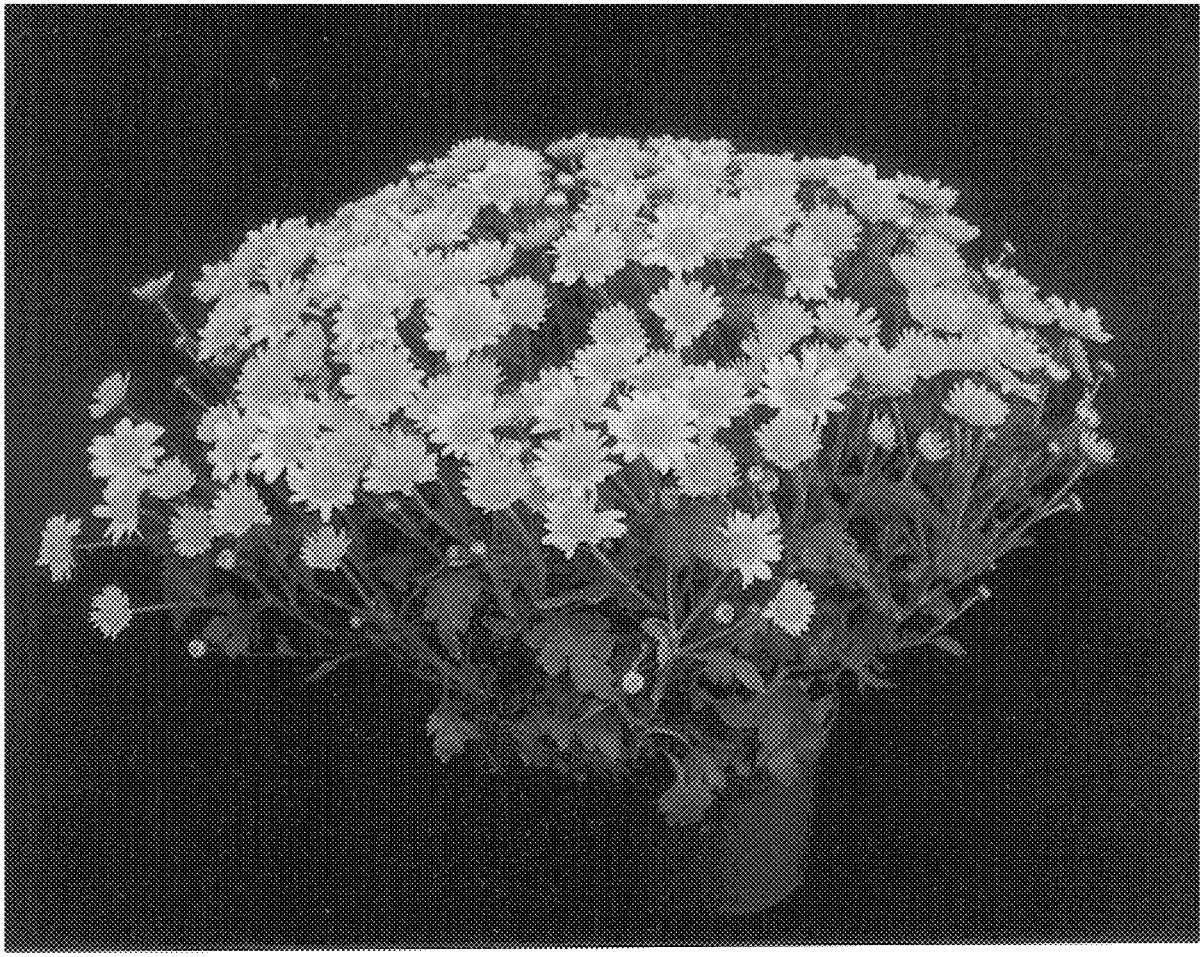
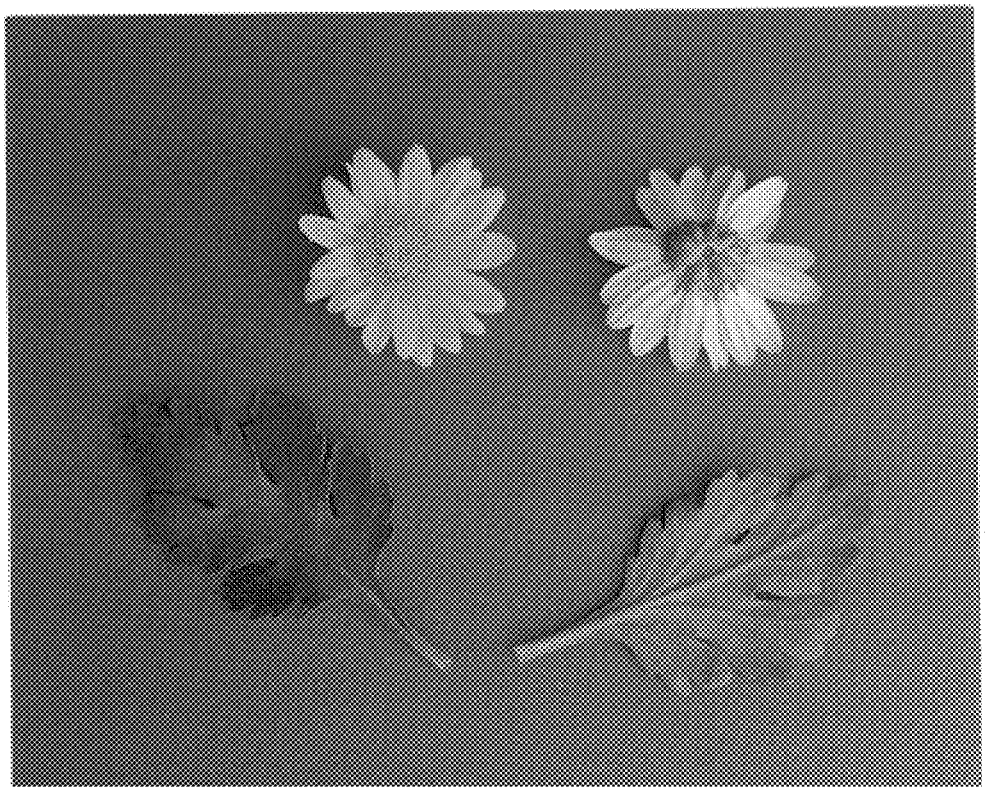

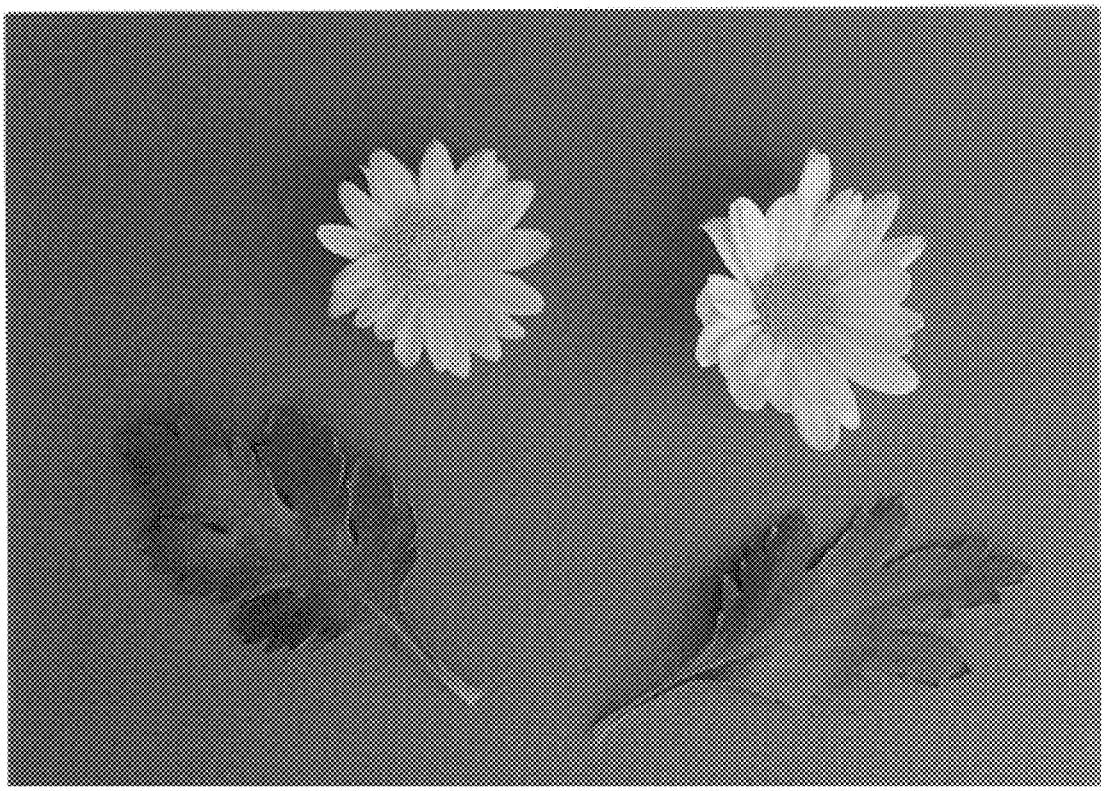

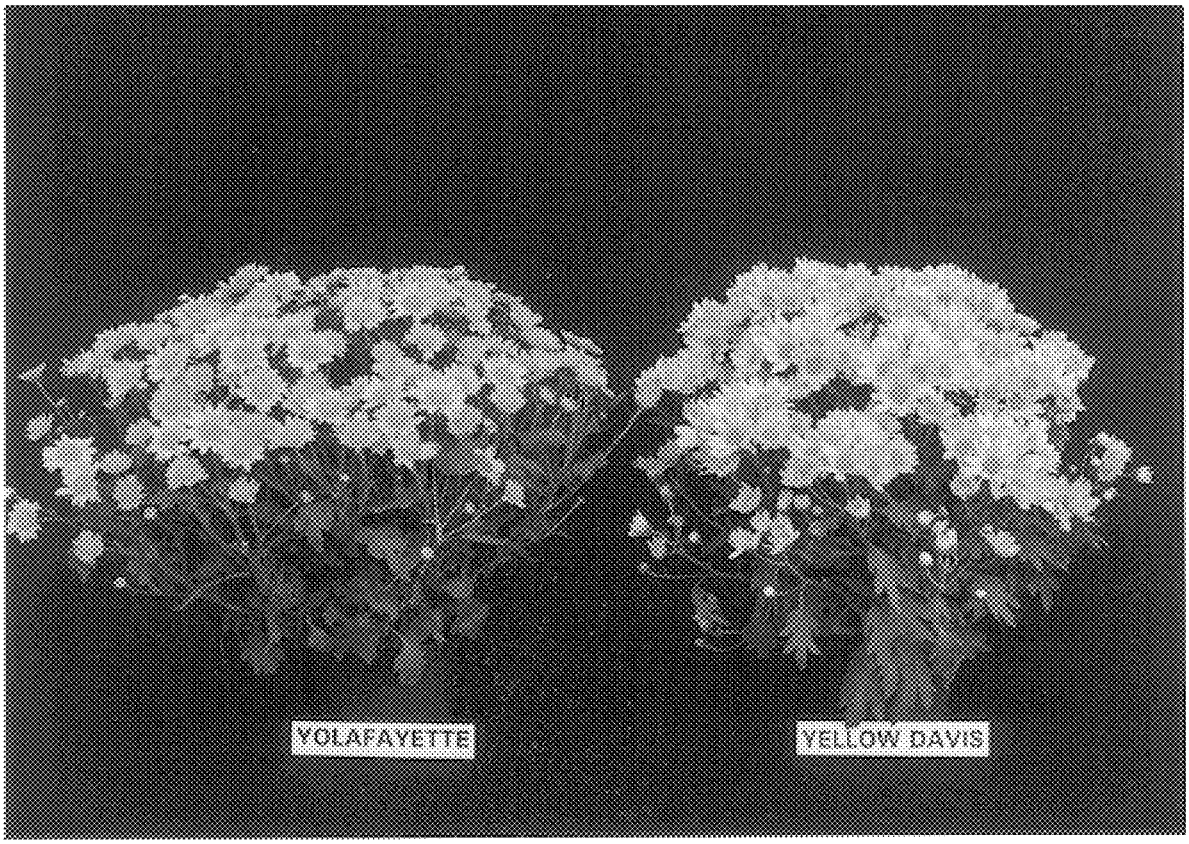
YOLAFAYETTE
YELLOW DAVIS